United States Patent [19]
Stokes

[11] Patent Number: 5,104,640
[45] Date of Patent: Apr. 14, 1992

[54] FIXATIVE COMPOSITION FOR FIXING BLOOD SMEARS TO SLIDES

[75] Inventor: Barry O. Stokes, Logan, Utah

[73] Assignee: Wescor, Inc., Logan, Utah

[21] Appl. No.: 325,524

[22] Filed: Mar. 17, 1989

[51] Int. Cl.$^5$ .............................................. G01N 1/00
[52] U.S. Cl. ........................................ 424/3; 435/4; 435/1; 435/29; 436/174
[58] Field of Search ................... 436/174, 175; 424/3; 420/40

[56] References Cited

U.S. PATENT DOCUMENTS

| | | | |
|---|---|---|---|
| 3,860,548 | 1/1975 | Roccheggiani et al. | 524/598 |
| 4,070,322 | 1/1978 | Hwang et al. | 524/104 |
| 4,578,282 | 3/1986 | Harrison | 436/527 |
| 4,783,337 | 11/1988 | Wong et al. | 424/468 |
| 4,857,300 | 8/1989 | Maksem | 435/4 |
| 4,859,604 | 8/1989 | Gould et al. | 436/15 |
| 4,946,669 | 8/1990 | Siegfried et al. | 422/40 |
| 4,970,034 | 11/1990 | Ly et al. | 210/500.41 |

*Primary Examiner*—David L. Lacey
*Assistant Examiner*—Thomas E. Daley
*Attorney, Agent, or Firm*—Mallinckrodt & Mallinckrodt

[57] ABSTRACT

A fixative solution for fixing biological smears, such as blood smears, to a slide for subsequent staining of the smear, which can be used in automated slide staining equipment, includes a fixative liquid, a stabilizing agent to reduce water spotting problems during fixing and/or to stabilize cellular components of the smear, and a solubilizing agent for maintaining the stabilizing agent in solution in the solubilizing agent after evaporation of the fixative liquid to thereby prevent formation of the solid residue normally formed by the stabilizing agent upon evaporation of the fixative liquid. The invention also includes the method fo preventing formation of a solid residue upon evaporation of the fixative liquid from a fixative liquid-stabilizing agent solution by the addition of a solubilizing agent thereto. The mixture of the stabilizing agent and solubilizing agent can be made as a concentrated additive to be added to a fixative liquid prior to use. The preferred stabilizing agent is polyvinyl pyrrolidone and the preferred solubilizing agent is ethylene glycol.

15 Claims, No Drawings

FIXATIVE COMPOSITION FOR FIXING BLOOD SMEARS TO SLIDES

BACKGROUND OF THE INVENTION

1. Field

The invention is in the field of fixing biological smears, such as blood smears, to slides for examination and evaluation.

2. State of the Art

There are currently various procedures used to fix biological smears, such as blood smears, on slides and then staining the smears so that certain components of the smears will take on certain characteristics and become visible to a person examining the smear. The fixing of the smear is usually necessary prior to staining so that the stain does not wash the smeared material from the slide.

It is currently normal practice with blood smears to place a smear on a slide and allow the smear to dry. The smear is then fixed on the slide by wetting the smear with anhydrous methanol and allowing the methanol to dry. The smear may be wetted with methanol by dipping, flooding, or spraying the slide. When the methanol evaporates or dries, the smear is fixed on the slide and subsequent staining of the smear does not remove the smear. The fixing of the smear and subsequent staining can be done manually, but there are several commercially available automated staining machines.

When fixing a blood smear on a slide in a humid atmosphere, there is a common problem with water condensing on the smear during fixing of the smear. The presence of water during methanol fixation produces refractile body artifacts (water spots) in the erythrocytes. These water spots persist through staining of the smear and cover items of interest in the smear. Further, they are distracting to the person evaluating the smear. In some cases, the water spots may interfere with diagnosis.

Another problem that occurs when fixing and staining blood smears is that some cellular components of the smear may be poorly preserved by the fixation. Because of this, these components may not show up adequately with subsequent staining of the smear.

A common practice to prevent water spotting of a smear and to stabilize cellular components is to add a stabilizing agent to the fixative liquid to form a fixative solution. A commonly used stabilizing agent, particularly when methanol is used as the fixative liquid, is polyvinyl pyrrolidone (PVP). PVP is commercially available and is a component in the commercially available blood smear fixative sold under the name Diff 3 Fixative System by Coulter Electronics of Hialeah, Fla.

Automated slide staining equipment is currently commercially available. The method of operation of such equipment varies with some equipment mechanically dipping a slide into a reservoir of the solution to be applied to the slide, such as a fixative liquid, otherwise passing the slide through such liquid to be applied, or otherwise mechanically flooding the slide with such liquid. In one commercially available automated slide stainer, sold under the trademark Aerospray by Wescor, Inc., Logan, Utah, slides to be stained are placed in the equipment and stain is sprayed onto the slides. The Aerospray incorporates an automatic fixing cycle so that slides with smears thereon are placed in the machine, a fixative liquid, such as methanol, is first sprayed onto the slides and allowed to evaporate to fix the smear, and then the stain is sprayed onto the slides to accomplish the staining. This equipment also contains a cleaning cycle in which the fixative liquid is used to flush out the staining nozzles. In this equipment, the spray compartment is usually cool and humid and water spotting during fixing can be a serious problem. While the fixative solutions using PVP or other stabilizers work well for hand fixing of smears and in automated equipment using dipping or similar methods for coating a slide, the PVP in its natural state is a solid material and when the methanol evaporates from the methanol-PVP solution, a hard plastic residue is formed. This can cause problems with the use of a methanol-PVP fixative solution, or any other similar fixative solution, in the automated slide staining equipment described wherein the fixative solution is sprayed onto the slides. Methanol is very volatile and evaporates rapidly leaving behind the solid residue. This can clog the nozzles of the equipment and/or distort the spray patterns of the nozzles thereby producing irregular staining or fixing results. It is thus not recommended to use stabilizing agents in fixative liquids used in such automated equipment. Current recommended procedure with such equipment is to fix the smear to the slides by hand so a stabilizing agent can be used without clogging the equipment and then perform the staining using the equipment.

It would be desireable to be able to use the indicated automated staining equipment for the whole process, i.e., the fixing of the smear as well as the staining of the smear, and, at the same time, avoid the water spotting problem during fixing of the smear and enable the stabilization of certain cellular components in the smear while not worrying about clogging the nozzles and passages of the equipment.

SUMMARY OF THE INVENTION

According to the invention, it has been found that the problems of water spotting and loss of cellular components associated with the fixing of a biological smear prior to staining the smear in automated staining equipment may be reduced by adding a stabilizing agent to the fixative liquid in normal manner and also adding a solubilizing agent which maintains the stabilizing agent in a fluid form and blocks solidification of the stabilizing agent in the equipment.

In a preferred form of the invention, the fixative liquid is methanol, the stabilizing agent is PVP, and may make up to about 2% by weight of the final fixative solution and the solubilizing agent is ethylene glycol, which may make up to about 10% by volume of the final fixative solution.

The addition of the solubilizing agent, eventhough it does not evaporate from the smear, does not interfere with the fixing of the smear to the slide and does not interfere with the later staining of the smear, and, importantly, keeps the stabilizing agent from solidifying to clog or plug the passages or nozzles of automated staining equipment and to allow easy cleanup of such equipment. By using the fixative solution of the invention, automated slide staining equipment may be used to automatically fix smears to the slides and then stain the slides.

The invention also contemplates the preparation of the stabilizing agent and solubilizing agent as a premixed, concentrated additive solution, to be added to a fixative liquid to form a final fixative solution which, in addition to fixing the smear on a slide, will stabilize cellular components and/or will reduce or prevent water spotting of the smear. Further, no solid residue is formed when the fixative liquid evaporates.

The method of the invention involves the steps of adding a stabilizing agent and a solubilizing agent to a fixative liquid to stabilize cellular components and/or to reduce or eliminate water spotting of a smear during fixing of the smear on a slide and, at the same time, to prevent the formation of a solid residue as the fixative liquid evaporates from the fixative solution. In addition, it involves the method of producing a stable, liquid additive to be added to a fixative liquid to produce the fixative solution of the invention. Preparation of the additive includes the steps of mixing a solubilizing agent and a stabilizing agent.

DETAILED DESCRIPTION OF THE PREFERRED EMBODIMENT

It has been found that an effective solution for use in fixing biological smears to stabilize cellular components and reduce or eliminating water spotting on the smears can be made by combining a fixative liquid, a stabilizing agent to stabilize cellular components and to reduce water spotting, and a solubilizing agent to maintain the stabilizing agent in a liquid form upon evaporation of the fixative liquid.

As indicated under the Background of the Invention, it is common practice to use a fixative liquid to fix a biological smear, such as a blood smear, on a slide in order to prepare the smear for later staining. The fixing prevents the smear material from dispersing over or running from the slide in the presence of the liquid stain applied to the smear during staining. Various fixative liquids may be used with the most widely used fixative liquid for blood smears being methanol. Other fixative liquids include ethanol, propanol, isopropanol, acetone, and formaldehyde. The fixative liquid is applied to the smear by either flooding or dipping the slide containing the smear into the fixative liquid, or with some automated staining equipment, such as with the automated staining equipment sold under the trademark Aerospray by Wescor, Inc., Logan Utah, by spraying the fixative liquid onto the slide and smear.

To stabilize cellular components and/or to reduce or eliminate water spotting problems during the fixing of the smear, it is common to add a stabilizing agent to the fixative liquid. Where these stabilizing agents are solids in their normal state, when the fixative liquid evaporates, the stabilizing agent returns to a solid state producing a solid residue. A particularly effective and commonly used stabilizing agent is polyvinyl pyrrolidone (PVP). PVP is used in the Diff 3 Fixation System available commercially from Coulter Electronics of Hialeah, Fla. Various other materials may also be used as stabilizers, such as polyethylene glycol (carbowax) either alone or in combination with PVP, as currently used in commercially available cytology fixatives, and malachite green or other dyes as sold by Fisher Scientific which can be used for stabilization.

As indicated above, with a fixative liquid-stabilizing agent solution, when the fixative liquid evaporates, the stabilizing agent forms a solid residue. This can create problems in automated equipment where a fixative liquid-stabilizing agent solution is sprayed by the equipment onto the slides having the smears thereon. This is because the fixative liquid usually evaporates quite rapidly. Any fixative liquid-stabilizing agent solution that remains in a nozzle, or in other passages where the fixative liquid can evaporate, will form a solid residue upon evaporation of the fixative liquid which can clog the nozzle and cause uneven spray patterns, or, in extreme cases, can even plug the nozzle or passage.

With the fixative solution of the invention, a solubilizing agent is also added to the solution in addition to the stabilizing agent. The solubilizing agent maintains the stabilizing agent in a liquid form after evaporation of the fixative liquid so there is no solid residue formed that will plug nozzles and passages in automated staining equipment. It has been found that although the stabilizing agent is kept in liquid form and not allowed to solidify, the smear is nonetheless fixed on the slide upon evaporation of the fixative and the liquid solution of stabilizing agent and solubilizing agent that remains on the smear does not interfere with the subsequent staining of the smear or later evaluation of the smear.

Various solubilizing agents may be used. The important properties of the solubilizing agent are a low viscosity, in the range of 1 to 50 centipoise, and preferably below 30 centipoise, so that it will not gum up spraying equipment nozzles and will spray satisfactory from such nozzles, and a boiling point at least that of water, i.e., 100° C., and preferably above 150° C., to slow evaporation. The solubilizing agent must also be soluble in the fixative liquid to at least the proportion of solubilizing agent to be included in the fixative solution, usually about 10% and preferably up to about 30% by volume, and it must have a solubility for the stabilizing agent of at least the proportion of stabilizing agent in the solubilizing agent upon evaporation of the fixative liquid from the fixative solution. This will generally be about 20% or less but preferably ranges up to about 50% to allow production of a concentrated additive. The solubilizing agent must also be soluble by the stain being used for staining of the smear so that it will not interfere with such staining. Thus, when aqueous based stains are used, as is normally the case, the solubilizing agent must be water soluble. The currently preferred solubilizing agent is ethylene glycol but diethylene glycol; propylene glycol; the various butanediols; methyl, ethyl, and butyl ethers of ethylene glycol and diethylene glycol; the acetate esters of ethylene glycol, diethylene glycol, and the ether derivatives thereof; furfuryl alchohol; tetrahydrofurfuryl alcohol; diacetone alcohol; N methyl 2-pyrrolidinone; N, N-dimethyformamide; γ butyrolactone; 1–4 Dioxane; or dimethyl sulfoxide could be used.

The fixative solutions may contain up to about 6% by weight of stabilizing agent and up to about 30% by volume of solubilizing agent with the fixative liquid making up the remainder of the final fixative solution. Currently preferred fixative solutions contain up to about 2% by weight of stabilizing agent and up to about 10% by volume of solubilizing agent. When using methanol as the fixative liquid, a satisfactory fixative solution is obtained by adding 10% by volume ethylene glycol and 2% by weight, or 20 grams/liter, PVP to the methanol fixative liquid. However, it currently appears that a substantially lower percentage of PVP can be used and still effectively prevent or reduce water spotting or stabilize various cell components. Generally, lower percentages of a stabilizing agent, where effective, will be preferred. Upon evaporation of the methanol, the non-volatile residue for the example given above consists of a solution of PVP in ethylene glycol at a concentration of about 200 grams per liter of solution. While the residue solution is somewhat viscous, it readily rinses from equipment nozzles and passages and other surfaces, so the equipment may be easily cleaned and nozzle and passage plugging is avoided.

A further advantage of the invention is that the stabilizing agent and the solubilizing agent may be made up into a premixed, concentrated solution which can be used as an additive to a fixative liquid to produce the final fixative solution of the invention. For such purpose, a concentrate of stabilizing agent in solubilizing agent can be prepared and this can then be mixed by the end user with the fixative. Thus, a concentrate of PVP-ethylene glycol solution may be prepared in advance at a central location. Because of the low flammability and low toxicity of the additive solution it can be easily shipped to an end user who mixes it with the locally available methanol or other fixative liquid to prepare the final fixative solution. This avoidsthe inconvenience and expense of shipping flammable materials, such as the final fixative solution, to an end user. The amount of stabilizing agent in the solubilizing agent depends upon the desired end concentration in the fixative solution. Therefore, if the final solution is to have 10% solubilizing agent and 2% stabilizing agent, 200 grams per liter of stabilizing agent would be mixed with the solubilizing agent to form the additive. Upon adding the additive to the fixative liquid so that the additive makes up 10% of the volume of the resulting fixative solution, the desired proportions are achieved. When using the preferred PVP and ethylene glycol components, the PVP can be dissolved in the ethylene glycol up to 500 grams per liter, or more, if desired, to provide a wide range of final, mixed concentrations in the final fixative solution. Concentrations of between 150 and 500 grams of PVP per liter of ethylene glycol have been used satisfactory as an additive for fixatives.

The invention includes the method of stabilizing cellular components and/or reducing or eliminating water spotting during fixing of a biological smear on a slide while also preventing the formation of a solid residue after fixing by adding both a stabilizing agent to the fixative liquid to prevent or reduce water spotting and to stabilize cellular components and a solubilizing agent to keep the stabilizing agent in a liquid form upon evaporation of the fixative liquid to prevent it from forming a solid residue. The invention further includes the method of producing a stable, liquid additive to be added to a fixative liquid to form the fixative solution of the invention. The additive is produced by adding a solubilizing agent to the stabilizing agent to yield a liquid additive solution.

While the stabilizing agent has been referred to as such and an indicated purpose for using the stabilizing agent is to stabilize various cellular components in a smear and preserve them for the subsequent staining of the smear, in many cases such stabilization is not a problem and the stabilizing agents' principal or even sole purpose is to reduce or prevent water spotting of the smear.

Whereas this invention is here illustrated and described with specific reference to embodiments thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. A substantially nonaqueous fixative composition for fixing a biological smear on a slide for subsequent staining of the smear, comprising a fixative liquid; a stabilizing agent that would in the absence of a solubilizing agent form a solid residue upon evaporation of the fixative liquid, said stabilizing agent reducing water spotting artifacts produced during the adhering of a blood smear; and a solubilizing agent for maintaining the stabilizing agent in solution upon evaporation of the fixative liquid, said solubilizing agent making up from about 10% to about 30% by volume of the fixative composition, whereby said composition causes a blood smear to adhere to a slide so that the smear will not wash off during subsequent staining of the smear, said composition being substantially nonaqueous so as not to interfere with the reduction in water spotting problems effected by the stabilizing agent.

2. A substantially nonaqueous fixative composition according to claim 1, wherein the stabilizing agent makes up to about 6% by weight of the fixative solution.

3. A substantially nonaqueous fixative composition according to claim 1, wherein the stabilizing agent makes up to about 2% by weight of the fixative solution and the solubilizing agent makes up to about 10% by volume of the fixative solution.

4. A substantially nonaqueous fixative composition according to claim 1, wherein the fixative liquid is methanol, the stabilizing agent is polyvinyl pyrrolidone which makes up to about 2% by weight of the fixative solution, and the solubilizing agent is ethylene glycol which makes up to about 10% by volume of the fixative solution.

5. A substantially nonaqueous fixative composition according to claim 1, wherein the stabilizing agent is selected from the group consisting of polyvinyl pyrrolidone, polyethylene glycol, a dye, or a combination thereof.

6. A substantially nonaqueous fixative composition according to claim 1, wherein the solubilizing agent is selected from the group consisting of ethylene glycol; diethylene glycol; propylene glycol; a butanediol; methyl, ethyl, and butyl ethers of ethylene glycol and diethylene glycol; the acetate esters of ethylene glycol, diethylene glycol, and the ether derivatives thereof; furfuryl alchohol; tetrahydrofurfuryl alcohol; diacetone alcohol; N methyl 2-pyrrolidinone; N, N-dimethyformamide; γ butyrolactone; 1-4 dioxane; and dimethyl sulfoxide.

7. An additive composition for addition to a fixative liquid that causes a blood smear to adhere to a slide, said additive composition comprising a stabilizing agent making up to about 50% by volume of the additive composition and reducing water spotting artifacts produced during the adhering of the blood smear; and a solubilizing agent for maintaining the stabilizing agent in solution so as to prevent the stabilizing agent from forming a solid residue upon evaporation of the fixative liquid, the resulting composition being substantially nonaqueous after the addition of said additive composition so as not to interfere with the reduction in water spotting problems effected by the stabilizing agent, said additive composition when diluted with a fixative liquid will cause a blood smear to adhere to a slide so as not to wash off during subsequent application of stains to the smear.

8. An additive composition according to claim 7, wherein the stabilizing agent makes up to about 50% by weight of the additive.

9. An additive composition according to claim 7, wherein the stabilizing agent is polyvinyl pyrrolidone and the solubilizing agent is ethylene glycol.

10. An additive composition according to claim 7, wherein the additive comprises between 150 and 500 grams of stabilizing agent for each 500 grams of solubilizing agent.

11. An additive composition according to claim 10, wherein the stabilizing agent is polyvinyl pyrrolidone and the solubilizing agent is ethylene glycol.

12. An additive composition according to claim 7, wherein the stabilizing agent is selected from the group consisting of polyvinyl pyrrolidone, polyethylene glycol, a dye, or a combination thereof.

13. An additive composition according to claim 7, wherein the solubilzing agent is selected from the group consisting of ethylene glycol; diethylene glycol; propylene glycol; a butanediol; methyl, ethyl, and butyl ethers of ethylene glycol and diethylene glycol; the acetate esters of ethylene glycol, diethylene glycol, and the ether derivatives thereof; furfuryl alcohol; tetrahydrofurfuryl alcohol; diacetone alcohol; N methyl 2-pyrrolidinone; N, N-dimethyformamide; $\gamma$ butyrolactone; 1-4 dioxane; and dimethyl sulfoxide.

14. A substantially nonaqueous fixative composition, comprising 64–99% of a fixative liquid; up to 6% of a stabilizing agent that would in the absence of a solubilizing agent form a solid residue upon evaporation of the fixative liquid, said stabilizing agent reducing water spotting artifacts produced during the adhering of the blood smear; and up to 30% of a solubilizing agent, whereby said composition causes a blood smear to adhere to a slide so that the smear will not wash off during subsequent staining of the smear, said composition being substantially nonaqueous so as not to interfere with the reduction in water spotting problems effected by the stabilizing agent.

15. A substantially nonaqueous fixative composition, comprising 88–99% of a fixative liquid; up to 2% of a stabilizing agent that would in the absence of a solubilizing agent form a solid residue upon evaporation of the fixative liquid, said stabilizing agent reducing water spotting artifacts produced during the adhering of a blood smear; and up to 30% of a solubilizing agent, whereby said composition causes a blood smear to adhere to a slide so that the smear will not wash off during subsequent staining of the smear, said composition being substantially nonaqueous so as not to interfere with the reduction in water spotting problems effected by the stabilizing agent.

* * * * *